US011186858B1

(12) United States Patent
Solacroup et al.

(10) Patent No.: US 11,186,858 B1
(45) Date of Patent: Nov. 30, 2021

(54) METHODS FOR INCREASING BIOSIMILARITY

(71) Applicant: FRESENIUS KABI DEUTSCHLAND GMBH, Bad Homburg (DE)

(72) Inventors: Thomas Solacroup, Blonay (CH); Matthieu Stettler, Vucherens (CH); Martin Jordan, Ecublens (CH); Hervé Broly, Chatel-St Denis (CH)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/533,419

(22) Filed: Aug. 6, 2019

Related U.S. Application Data

(63) Continuation of application No. 15/457,651, filed on Mar. 13, 2017, now abandoned.

(60) Provisional application No. 62/308,641, filed on Mar. 15, 2016.

(51) Int. Cl.
*C12P 21/02* (2006.01)
*C07K 16/24* (2006.01)

(52) U.S. Cl.
CPC ............ *C12P 21/02* (2013.01); *C07K 16/241* (2013.01); *C07K 2317/14* (2013.01); *C07K 2317/51* (2013.01); *C07K 2317/515* (2013.01)

(58) Field of Classification Search
CPC . C12P 21/02; C07K 16/241; C07K 2317/515; C07K 2317/14; C07K 2317/51
See application file for complete search history.

(56) References Cited

U.S. PATENT DOCUMENTS

| 7,294,481 | B1 | 11/2007 | Fung |
| 8,084,032 | B2 | 12/2011 | Yumioka et al. |
| 8,895,709 | B2 | 11/2014 | Hickman et al. |
| 2005/0107594 | A1 | 5/2005 | Sun et al. |
| 2006/0030696 | A1 | 2/2006 | Bonnerjea et al. |
| 2006/0257972 | A1 | 11/2006 | Ishihara |
| 2010/0330071 | A1 | 12/2010 | Teschner et al. |
| 2014/0005368 | A1 | 1/2014 | Helman et al. |
| 2014/0148585 | A1 | 5/2014 | Sugihara et al. |
| 2015/0110775 | A1 | 4/2015 | Subramanian et al. |
| 2015/0267237 | A1 | 9/2015 | Meier et al. |
| 2016/0376304 | A1 | 12/2016 | Bertl et al. |
| 2019/0002822 | A1 | 1/2019 | Vijayasankaran et al. |

FOREIGN PATENT DOCUMENTS

| WO | 9622792 A1 | 8/1996 |
| WO | WO 2005/092926 | * 10/2005 |
| WO | 2015131978 A1 | 9/2015 |
| WO | 2016110227 A1 | 7/2016 |
| WO | 2016153191 A1 | 9/2016 |

OTHER PUBLICATIONS

Martens et al., "Configuration of Bioreactors"; Animal Cell Biotechnology: Methods and Protocols, Methods in Molecular Biology, vol. 1104; Chapter 19, pp. 285-311. Portner, Ralf (Ed); Humana Press (2014).
Boscolo, S. et al., "Simple Scale-up of Recombinant Antibody Production using an UCOE Containing Vector"; New Biotechnology (2012); vol. 29:4; pp. 477-484.
Cameron, R. et al., "Virus Clearance Methods Applied in Bioprocessing Operations: an Overview of Selected Inactivation and Removal Methods"; Pharmaceutical Bioprocessing (2014); vol. 2:1; pp. 78-83.
Sekine, S. et al., "Integrity Testing of Planova BioEx Virus Removal Filters used in the Manufacture of Biological Products"; Biologicals (2015); vol. 43; pp. 186-194.
Wendling, D. et al., "Paradoxical Effects of Anti-TNF-α agents in Inflammatory Diseases"; Expert Reviews in Clinical Immunology (2014); vol. 10:1; pp. 159-169.

* cited by examiner

*Primary Examiner* — Delia M Ramirez
(74) *Attorney, Agent, or Firm* — Fox Rothschild LLP

(57) ABSTRACT

The present invention relates to a method of increasing biosimilarity of a TNF α binding protein to a reference TNF α binding protein by modifying the charge profile of the binding protein produced by cell culture in a cell culture medium, by making an adjustment to a cell culture condition The adjustment is an increase in the concentration of a metal ion in the cell culture medium and the adjustment occurs on one or more days during the cell culture method, whereby the adjustment in the cell culture condition results in the modification of the charge profile of the binding protein. The present invention also relates to a biosimilar protein obtainable by such a process.

7 Claims, 3 Drawing Sheets
Specification includes a Sequence Listing.

METHODS FOR INCREASING BIOSIMILARITY

BACKGROUND OF THE INVENTION

A similar biological or 'biosimilar' medicine is a biological medicine that is similar to another biological medicine (the reference protein) that has already been authorised for use. It is important that biosimilars do not have any meaningful differences from the reference medicine in terms of quality, safety or efficacy.

In recombinant protein manufacturing, the final structure of the product is highly dependent on post-translational modifications that can occur during fermentation, as well as other modifications caused by the manufacturing process. These must be characterized and controlled. Impurities, particularly those that may induce an immunologic reaction, must be identified, characterized, and minimized in the final product. Proper formulation of the protein drug is also important, in order to minimize degradation and loss of potency over time, which can be caused by chemical changes such as oxidation and hydrolysis. Accurate and reproducible characterisation is therefore a requirement of the manufacturing process and product formulation of a protein therapeutic.

Biologics are often heterogeneous mixtures of closely related molecular weights and charged isoforms. Since they are derived from living cells, they typically include a complex pattern of impurities that form during all stages of production. In addition, recombinant proteins undergo complex post-translational modifications, have a highly specific three dimensional structure that depends in part on disulfide bridges, and have the potential for aggregation, adsorption, and truncation. Knowing the chemical, physical, and conformational characteristics of a protein is essential to understand its heterogeneity, impurity profile, and potency, such as the precise amino acid sequence, molecular weight, charge variances, glycosylation, aggregation level, and oxidation level. These changes may not only impact stability but also activity, and they can cause immunologically adverse reactions. Hence, maintaining the profile of charge isoforms in therapeutic protein preparations is key during the development and manufacturing processes.

Monoclonal antibodies in particular are well established pharmacological therapeutic molecules used for the treatment of certain diseases including inflammatory, oncology and autoimmune diseases. Heterogeneity of purified antibodies (immunoglobulins) based on simple chemical modifications of selected amino acids within the monoclonal antibody sequence is of considerable importance in the pharmaceutical/biotechnology field. Many proteins, including antibodies have charged heterogeneity that optimises the balance of allowing them to achieve structural stability, binding affinity, chemical properties and biological reactivity. Changes in the charge profile/heterogeneity can therefore affect the pharmacokinetics of an antibody composition even if produced from a homogeneous cell culture.

One such charge profile is exemplified in WO 2014/159554. Examples of variants within a charge profile include acidic variants such as sylation, deamidation, C-terminal lysine cleavage, and basic variants such as acylation, cysteine, lysine, histidine or tryptophan oxidation or C-terminal lysine and glycine amidation. WO 2014/159554 describes a low acidic species (low AR) composition comprising an antibody, which has about 15% or less AR wherein the AR contains a first acidic species region AR1 and a second acidic species region AR2.

SUMMARY OF THE INVENTION

The present invention provides a cell culture method of increasing biosimilarity of a TNF α binding protein to a reference TNF α binding protein by modifying the charge profile of the binding protein produced by cell culture in a cell culture medium, the method comprising making an adjustment to least one cell culture condition wherein the adjustment is an increase in the concentration of a metal ion in the cell culture medium and wherein the adjustment occurs on one or more days during the cell culture method, whereby the adjustment in the cell culture condition results in the modification of the charge profile of the binding protein.

In an embodiment of the present invention, the cell culture method is a fed-batch culture method. In an embodiment of the present invention, the cell culture method has a duration of up to 17 days. In an embodiment of the present invention, a further adjustment is made to a cell culture condition, selected from decreasing the pH of the cell culture medium in the cell culture medium. In an embodiment of the present invention, the metal ion is selected from the group consisting of Fe, Cu, Zn and Se. In an embodiment of the present invention, the pH is decreased by the addition of an acid to the cell culture medium. In an embodiment of the present invention, the decrease of pH is achieved with increasing the concentration of $CO_2$ in the cell culture.

In an embodiment of the present invention, wherein the TNF α binding protein is an antibody. In an embodiment of the present invention, the antibody is adalimumab, infliximab or a biosimilar thereof. In an embodiment of the present invention, the antibody is adalimumab or a biosimilar thereof, wherein the antibody has: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine. In an embodiment of the present invention, the TNF α binding protein is etanercept or a biosimilar thereof.

In an embodiment of the present invention, the culture of cells is a culture of CHO cells. In an embodiment of the present invention, the cells are CHO-S cells. In an embodiment of the present invention, the concentration of the metal ion or the concentration of the amino acid is increased by way of adding a feed medium comprising the metal ion or amino acid to the culture medium on one or more of day 3, 4, 5, 6, 7, 8, 9, 10, 11, 12, 13 or 14 of the cell culture method. In an embodiment of the present invention, the concentration of the metal ion and/or the amino acid is adjusted on one or more of days 3, 5, 7, 10 and 14. In an embodiment of the present invention, the concentration of Fe is increased by adding Fe to a concentration of between about 0.5 g/L and about 5.0 g/L, in addition to any Fe already present in the cell culture medium. In an embodiment of the present invention, the concentration of Cu is increased by adding Cu to a concentration of between about 100 nM and about 1000 nM, in addition to any Cu already present in the cell culture medium. In an embodiment of the present invention, the concentration of Zn is increased by adding Zn at a concentration of between about 1 µM and about 30 µM, in addition to any Zn already present in the cell culture medium. In an embodiment of the present invention, the concentration of Se is increased by adding Se to a concentration of between about 5 nM and 100 nM, in addition to any Se already present in the cell culture medium. In an embodiment of the present invention, the pH is decreased on one or more of day 3, 4, 5, 6, 7, 8, 9, 10, 11, 12 or 13. In an embodiment of the present invention, the charge profile of the TNF α binding protein is modified such that: (i) the level of acidic variants of the TNF α binding protein is within 20% of the level of acidic variants of the reference protein; (ii) the level of main peak species of the TNF α binding protein is within 20% of the level of main peak species of the reference protein; and (iii) the level of basic variants of the TNF α binding protein is within 20% of the level of basic variants of the reference protein. In an embodiment of the present invention, the reference protein is an antibody. In an embodiment of the present invention, the reference protein is Humira®. In an embodiment of the present invention, the cell culture medium is serum-free. In an embodiment of the present invention, the cell culture medium is protein free.

The present invention also provides a recombinant protein obtainable by any of the above mentioned methods. In an embodiment of the present invention, the recombinant protein is a TNF α binding protein. In an embodiment of the present invention, the TNF α binding protein is an antibody. In an embodiment of the present invention, the antibody is adalimumab or a biosimilar thereof, wherein the antibody has: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a pharmaceutical composition comprising any of the above mentioned recombinant proteins. In an embodiment of the present invention, the recombinant protein is an adalimumab biosimilar. In an embodiment of the present invention, the recombinant protein is an antibody having: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present also provides a method of producing a protein comprising growing a host cell in a cell culture medium, expressing the protein in the host cell, making an adjustment to least one cell culture condition wherein the adjustment is an increase in the concentration of a metal ion in the cell culture medium and wherein the adjustment occurs on one or more days during the cell culture method, whereby the adjustment in the cell culture condition results in the modification of the charge profile of the binding protein, and purifying the protein from the cell culture.

In an embodiment of the present invention, the cell culture method is a fed-batch culture method. In an embodiment of the present invention, the cell culture method has a duration of up to 17 days. In an embodiment of the present invention, a further adjustment is made to a cell culture condition, selected from decreasing the pH of the cell culture medium in the cell culture medium. In an embodiment of the present invention, the metal ion is selected from the group consisting of Fe, Cu, Zn and Se. In an embodiment of the present invention, the pH is decreased by the addition of an acid to the cell culture medium. In an embodiment of the present invention, the decrease of pH is achieved with increasing the concentration of $CO_2$ in the cell culture.

In an embodiment of the present invention, the protein is a TNF α binding protein. In an embodiment of the present invention, the TNF α binding protein is an antibody. In an embodiment of the present invention, the antibody is adalimumab, infliximab or a biosimilar thereof. In an embodiment of the present invention, the antibody is adalimumab or a biosimilar thereof, wherein the antibody has: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine. In an embodiment of the present invention, the TNF α binding protein is etanercept or a biosimilar thereof.

In an embodiment of the present invention, the culture of cells is a culture of CHO cells. In an embodiment of the present invention, the cells are CHO-S cells. In an embodiment of the present invention, the concentration of the metal ion or the concentration of the amino acid is increased by way of adding a feed medium comprising the metal ion or amino acid to the culture medium on one or more of day 3, 4, 5, 6, 7, 8, 9, 10, 11, 12, 13 or 14 of the cell culture method. In an embodiment of the present invention, the concentration of the metal ion and/or the amino acid is adjusted on one or more of days 3, 5, 7, 10 and 14. In an embodiment of the present invention, the concentration of Fe is increased by adding Fe to a concentration of between about 0.5 g/L and about 5.0 g/L, in addition to any Fe already present in the cell culture medium. In an embodiment of the present invention, the concentration of Cu is increased by adding Cu to a concentration of between about 100 nM and about 1000 nM, in addition to any Cu already present in the cell culture medium. In an embodiment of the present invention, the concentration of Zn is increased by adding Zn at a concentration of between about 1 µM and about 30 µM, in addition to any Zn already present in the cell culture medium. In an embodiment of the present invention, the concentration of Se is increased by adding Se to a concentration of between about 5 nM and 100 nM, in addition to any Se already present in the cell culture medium. In an embodiment of the present invention, the pH is decreased on one or more of day 3, 4, 5, 6, 7, 8, 9, 10, 11, 12 or 13. In an embodiment of the present invention, the charge profile of the TNF α binding protein is modified such that: (i) the level of acidic variants of the TNF α binding protein is within 20% of the level of acidic variants of the reference protein; (ii) the level of main peak species of the TNF α binding protein is within 20% of the level of main peak species of the reference protein; and (iii) the level of basic variants of the TNF α binding protein is within 20% of the level of basic variants of the reference protein. In an embodiment of the present invention, the cell culture medium is serum-free. In an embodiment of the present invention, the cell culture medium is protein free.

The present invention also provides a recombinant protein obtainable by any of the above mentioned methods of making. In an embodiment of the present invention, the recombinant protein is a TNF α binding protein. In an embodiment of the present invention, the TNF α binding protein is an antibody. In an embodiment of the present invention, the antibody is adalimumab or a biosimilar thereof, wherein the antibody has: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a pharmaceutical composition comprising any of the above mentioned recombinant proteins. In an embodiment of the present invention, the recombinant protein is an adalimumab biosimilar. In an embodiment of the present invention, the recombinant protein is an antibody having: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

DETAILED DESCRIPTION

Figure 1:
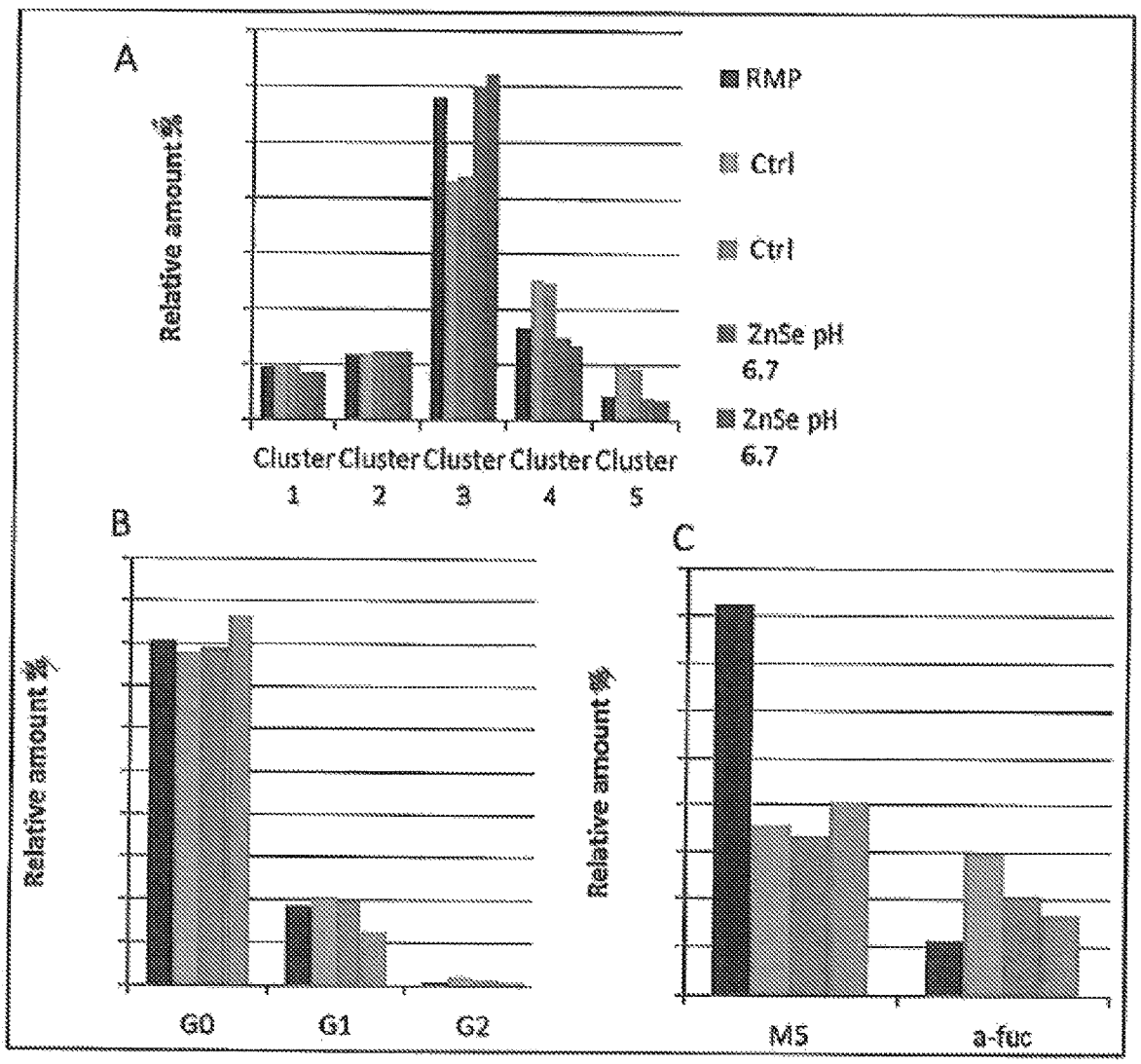
FIG. 1 shows the impact of Zinc and selenium on charge profile.

As known in the art, a biosimilar product will not be identical to the reference protein due to many factors, including fact that proteins produced in different mammalian cell lines or under different environmental conditions may be expressed with subtle but important differences with respect to certain characteristics of the protein, e.g. the level of acidic variants, the level of main peak species, the level of basic variants. For this reason biosimilars are never assumed to be exact copies of the reference protein and therefore cannot be directly approved on that basis by authorities, such the Food and Drug Agency (FDA) or the European Medicines Agency (EMA). Provided that a biosimilar can be shown to fall within a "biosimilar corridor" of levels of characteristics of the reference protein, it is generally accepted that the biosimilar may be similar enough to the reference protein to gain approval from the authorities. A "biosimilar corridor" is established by testing characteristics of different batches of the reference protein. For example, Humira® manufactured by Abbvie, (adalimumab), was released in 2003 following approval on 31 Dec. 2002. In the intervening years, very slight differences have been found in subsequent batches of Humira® due to completely usual changes in manufacturing processes and manufacturing sites. By measuring the characteristics of different batches of reference protein, a "biosimilar corridor" can be established. Characteristics that are assessed include the level of acidic variants, the level of main peak species, the level of basic variants, the glycosylation variants, aggregates and fragments of the reference protein. A range of levels associated with each characteristic can be established to build the biosimilar corridor. The present invention relates to a cell culture method of increasing biosimilarity of a TNF α binding protein to a reference TNF α binding protein by modifying the charge profile of the binding protein produced by cell culture in a cell culture medium, the method comprising making an adjustment to least one cell culture condition wherein the adjustment is an increase in the concentration of a metal ion in the cell culture medium and wherein the adjustment occurs on one or more days during the cell culture method, whereby the adjustment in the cell culture condition results in the modification of the charge profile of the binding protein.

By increasing biosimilarity, it is meant that certain characteristics of the protein are brought as close as possible to the characteristics of the reference protein. Such characteristics include, but are not limited to, the charge profile of the protein, which includes acidic variants, a main peak species (the majority of the protein, when assessed by charge) and basic variants.

In embodiments of the present invention, the charge profile i.e. the balance of acidic species, main species, and basic species, of a protein produced by a culture of cells in a fed-batch culture may be influenced by many factors such as available nutrients, temperature, pH, oxygenation, length of culture period, cell density, size of culture and type of cell. If a particular charge profile is desired, certain cell conditions can be adjusted in order to achieve a target charge profile.

The present invention also provides a method of producing a protein comprising expressing the protein in a host cell growing in a cell culture medium, making an adjustment to least one cell culture condition wherein the adjustment is an increase in the concentration of a metal ion in the cell culture medium and wherein the adjustment occurs on one or more days during the cell culture method, whereby the adjustment in the cell culture condition results in the modification of the charge profile of the binding protein, and purifying the protein from the cell culture.

In embodiments of the present invention, the metal ion may be selected from the group consisting of Fe, Cu, Zn and Se.

In embodiments of the present invention, the concentration of Fe may be increased by added Fe to a concentration of between about 0.5 g/L and about 5 g/L or about 0.9 g/L and about 3 g/L, in addition to any Fe already present in the cell culture medium.

In embodiments of the present invention, the concentration of Cu may be increased by adding Cu to a concentration of between about 100 nM and about 1000 nM or about 125 nM and about 725 nM, in addition to any Cu already present in the cell culture medium.

In embodiments of the present invention, the concentration of Zn may be increased by adding Zn to a concentration of between about 1 µM and about 30 µM or about 5 µM and about 20 µM, in addition to any Zn already present in the cell culture medium.

In embodiments of the present invention, the concentration of Se may be increased by adding Se to a concentration of between about 5 nM and about 100 nM or about 10 nM and about 80 nM, in addition to any Se already present in the cell culture medium.

In embodiments of the present invention, the cell culture condition may be adjusted by increasing the concentration of one or more amino acids in the cell culture medium. In some embodiments, the amino acid may be selected from the group consisting of asparagine, cysteine and tyrosine.

In embodiments of the present invention, the concentration of the metal ion and/or the concentration of the amino acid is increased by way of a feed medium added to the culture medium on one or more of day 3, 4, 5, 6, 7, 8, 9, 10, 11, 12, 13 or 14 of the cell culture method. The feed medium may be added on one or more of days 3, 5, 7, 10 and 14. The concentration of the metal ion and/or the amino acid may be increased by the addition of one or more of the metal ions or amino acids as separate additions to the feed medium, on the same or on a different day to the feed medium.

In embodiments of the present invention, the pH of the cell culture medium may be adjusted. In some embodiments, the adjustment to the pH may mean that the pH is decreased. Such a decrease of pH may be achieved by the use of $CO_2$, in particular, by increasing the concentration of CO2 in the cell culture medium. In embodiments of the present invention, the increased CO2 concentration may be up to 20%. In some embodiments, the pH may be decreased on one or more of day 3, 4, 5, 6, 7, 8, 9, 10, 11, 12 or 13, and may be maintained at the lower pH for the remaining duration of the cell culture.

In embodiments of the present invention, the TNFα binding protein may be a biosimilar of an antibody. In some embodiments, the antibody may be a biosimilar of adalimumab or infliximab. In some embodiments, the TNFα binding protein may be a biosimilar of etenercept.

In an embodiments of the present invention, the culture of cells may be a culture of eukaryotic cells. In some embodiments, the culture of cells may be a culture of mammalian cells. In other embodiments, the culture of cells may be a culture of CHO cells. In some embodiments, the culture of cells may be CHO-S Cells.

In embodiments of the present invention, the charge profile may be modified such that the level of acidic variants, the main peak species and the basic variants are within 20% of the levels of the reference protein.

In some embodiments, the reference protein may be Humira®.

In embodiments of the present invention, the cell culture medium may be serum-free and/or protein free.

The present invention relates to a method of controlling the charge profile of a recombinant protein, by adjusting at least one cell culture condition, which results in a change in the charge profile of the recombinant protein produced by the culture of cells.

In particular, the inventors have found that certain conditions influence the charge profile in such a way that it becomes more similar to a reference protein's charge profile, for example that described in WO 2014/159554. Conditions that may be adjusted include a metal ion concentration, the pH of the cell culture medium or a concentration of certain amino acids within the cell culture medium.

As used herein, the term "acidic species", and "basic species" and "main peak/species" refer to a characteristic of a population of proteins which are identifiable by methods well known to one skilled in the art, for example, by chromatography electrophoresis and mass spectrometry techniques. As mentioned above, acidic variants include sialylation, deamidation, C-terminal lysine, di-sulphide reduced variants, non-reducible variants. More than one acidic and/or basic species can be present in particular a first acidic species and a second acidic species.

The acidic species are generally represented in a peak to the left of the main peak and the basic species to the right of the main peak. The two smaller peaks are generally formed of deamination and glycosylation products although other isoforms may be present.

As used herein, the term "about" or "approximately" has its general meaning as understood to one of skill in the art within the context of the referenced value or range. In some embodiments, as understood to one of skill in the art, the term "about" or "approximately" means within 20%, 15%, 10%, 9%, 8%, 7%, 6%, 5%, 4%, 3%, 2%, 1%, 0.5%, or 0.05% of a given value or range.

The term "amino acid" as used herein refers to any of the twenty naturally occurring amino acids that are normally used in the formation of polypeptides, or analogues or derivatives of those amino acids as understood by the skilled person. Amino acids of the present invention are provided in medium to cell cultures. The amino acids provided in the medium may be provided as salts or in hydrate form.

The term "antibody" is used as understood in the art, i.e. an immunoglobulin molecule that recognises and specifically binds to a target, such as a protein, polypeptide, peptide, carbohydrate, polynucleotide, lipid, or combinations of the foregoing etc., through at least one antigen recognition site within the variable region of the immunoglobulin molecule. The term encompasses, as understood in the art, intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of IgA, IgD, IgE, IgG, and IgM, and include, for example IgG1, IgG2, IgG3, IgG4, IgA1 and IgA2.

The term "cell culture medium" as used herein refers to any cell culture medium used to culture cells that has not been modified either by supplementation, or by selective removal of a certain component.

The term "batch culture" as used herein refers to a method of culturing cells in which all the components that will ultimately be used in culturing the cells, including the medium as well as the cells themselves, are provided at the beginning of the culturing process i.e. day 0. A batch culture is typically stopped at some point and the cells and/or components in the medium are harvested and optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 liter and may be 10, 100, 250, 500, 1000, 2500, 5000, 8000, 10,000, 12,000, 15,000 litres or more, or any volume in between. The internal conditions of the bioreactor are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of the large-scale cell culture production bioreactor is typically at least 500 liters and may be 1000, 2000, 2500, 5000, 8000, 10,000, 12,0000 liters or more, or any volume in between. One of ordinary skill in the art will be aware of and will be able to choose suitable bioreactors for use in practicing the present invention.

As used herein, "biosimilar" (of an approved reference product/biological drug, such as a protein therapeutic, antibody, etc.) refers to a biologic product that is highly similar to a reference product notwithstanding minor differences in clinically inactive components having no clinically meaningful differences between the biological product and the reference product in terms of the safety, purity, and potency of the product. In one embodiment, the biosimilar biological product is biosimilar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

The term "cell density" as used herein refers to that number of cells present in a given volume of medium.

The terms "culture", "cell culture" and "eukaryotic cell culture" as used herein refer to a eukaryotic cell population that is suspended in a medium under conditions suitable to survival and/or growth of the cell population. As will be clear to those of ordinary skill in the art, these terms as used herein may refer to the combination comprising the mammalian cell population and the medium in which the population is suspended.

The term "fed-batch culture" as used herein refers to a method of culturing cells in which additional components are provided to the culture at some time subsequent to the beginning of the culture process i.e. after day 0. The provided components typically comprise nutritional supplements for the cells which have been depleted during the culturing process. A fed-batch culture is typically stopped at some point and the cells and/or components in the medium are harvested and optionally purified.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. For a particular cell line, the period of time and conditions are determined to be optimal for cell growth and division. During the growth phase, cells are cultured in nutrient medium containing the necessary additives, in a controlled atmosphere, such that optimal growth is achieved for the particular cell line. Cells are maintained in the growth phase for a period of about between one and four days, usually between two to three days.

"Production phase" of the cell culture refers to the period of time during which cell growth has plateaued. During the production phase, logarithmic cell growth has ended and protein production is primary. During this period of time the medium is generally supplemented to maintain cell inability.

The term "expression" or "expresses" are used herein to refer to transcription and translation occurring within a host cell. Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The terms "cell culture medium", "culture medium", and "growth medium" as used herein refer to a solution containing nutrients which nourish growing eukaryotic cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined medium" such as a serum-free medium and/or protein free medium that contains no proteins, hydrolysates or components of unknown composition. Defined media are free of animal-derived components and all components have a known chemical structure. The term "protein-free" is intended to mean that no protein supplements are added to the cell culture medium before or during the cell culture process.

The terms "protein" as used herein refers to a sequential chain of amino acids linked together via peptide bonds, also referred to interchangeably with the term "polypeptide". The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit. If discrete functional unit is comprised of more than one polypeptide that physically associate with one another, the term "protein" as used herein refers to the multiple polypeptides that are physically coupled and function together as the discrete unit, such as an antibody.

"Recombinantly expressed polypeptide" and "recombinant polypeptide protein" as used herein refer to a polypeptide expressed from a mammalian host cell that has been genetically engineered to express that polypeptide. The recombinantly expressed polypeptide can be identical or similar to polypeptides that are normally expressed in the mammalian host cell. The recombinantly expressed polypeptide can also be foreign to the host cell (i.e. exogenous). Alternatively, the recombinantly expressed polypeptide can be chimeric in that portions of the polypeptide contain amino acid sequences that are identical or similar to polypeptides normally expressed in the mammalian host cell, while other portions are foreign to the host cell.

The term "titre" as used herein refers to the total amount of recombinantly expressed polypeptide or protein produced by a mammalian cell culture divided by a given amount of medium volume. Titre is typically expressed in units of milligrams of polypeptide or protein per milliliter of medium.

As used herein, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

Those of ordinary skill in the art will understand that various modifications to these preferred embodiments are within the scope of the appended claims. It is the claims and equivalents thereof that define the scope of the present invention, which is not and should not be limited to or by this description of certain preferred embodiments.

Any polypeptide or protein that is expressible in a host cell may be produced in accordance with the method of the present invention. The polypeptide is preferably expressed from a gene that is introduced into the host cell through genetic engineering, i.e. a recombinant polypeptide. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Of particular relevance to the present invention is the production of antibodies. Antibodies are proteins that have the ability to specifically bind a particular antigen. Any antibody that can be expressed in a host cell may be used in accordance with the present invention. In one embodiment, the antibody to be expressed is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can be produced by any method known to one of skill in the art.

In one embodiment, the methods of the invention are used to produce an antibody that specifically binds a tumour-necrosis factor (TNF)-$\alpha$. The antibody may be adalimumab, etanercept, or infliximab, or biosimilars thereof. Adalimumab is sold under the trade name Humira® and has CAS designation 33-1731-18-1. As used herein, "etanercept" refers to any fusion protein that inhibits a TNF$\alpha$, is sold under the trade name Enbrel®, and has Chemical Abstracts Service (CAS) designation number 185243-69-0. As used herein, "infliximab" refers to any chimeric monoclonal antibody that specifically binds to TNFα, is sold under the trade names Remicade®, Remsima®, and/or Inflectra®, and has CAS designation number 170277-31-3.

In an embodiment of the present invention, the TNFα antibody has (i) a light chain sequence of SEQ ID NO: 1 and a heavy chain sequence of SEQ ID NO: 2, or (ii) a light chain sequence having at least 90% identity with SEQ ID NO:1 and a heavy chain sequence having at least 90% identity with SEQ ID NO:2, or (iii) a light chain sequence having at least 95% identity with SEQ ID NO:1 and a heavy chain sequence having at least 95% identity with SEQ ID NO:2, particularly including adalimumab or a biosimilar thereof. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine. In an embodiment of the present invention, the TNFα binding protein may be a TNFα antibody, wherein the antibody is infliximab or a biosimilar thereof.

The term "biosimilar" (also known as follow-on biologics) is well known in the art, and the skilled person would readily appreciate when a protein would be considered a biosimilar of adalimumab. Furthermore, such "biosimilars" would need to be officially approved as a "biosimilar" for marketing before said "biosimilar" is sold on the open market. The term "biosimilar" is generally used to describe subsequent versions (generally from a different source) of reference proteins (whose drug substance is made by a living organism or derived from a living organism or through recombinant DNA or controlled gene expression methodologies) that have been previously officially granted marketing authorisation. Since reference proteins have a high degree of molecular complexity, and are generally sensitive to changes in manufacturing processes (e.g. if different cell lines are used in their production), and since manufacturers of biosimilars generally do not have access to the originator's molecular clone, cell bank, know-how regarding the fermentation and purification process, nor to the drug substance itself (only the innovator's commercialized drug product), any "biosimilar" is unlikely to be exactly the same as the innovator drug product.

In embodiments of the present invention, the antibody is an antigen-binding fragment of a full length antibody, e.g., a Fab, F(ab')2, Fv or a single chain Fv fragment. In some embodiments, the antibody is a full length antibody. The antibody can be a monoclonal antibody or a mono-specific antibody. In some embodiments, the antibody can be a human, humanized, CDR-grafted, chimeric, mutated, affinity matured, deimmunized, synthetic or otherwise in vitro-generated antibody, and combinations thereof.

Any mammalian cell or cell type susceptible to cell culture, and to expression of polypeptides, may be utilized in accordance with the present invention as known in the art. In embodiments of the present invention, the methods may be applied in the culturing of and expression of polypeptides from CHO cell lines. In some embodiments, the cell line may be CHO-2.

Additionally, any number of commercially and non-commercially available hybridoma cell lines that express polypeptides or proteins may be utilized in accordance with the present invention.

The mammalian cell culture of the method of the present invention may be prepared in any medium suitable for the particular cell being cultured. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions, as well as any media that are well known to the person skilled in the art. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and glucose or an equivalent energy source. Any other necessary supplements may also be included at appropriate concentrations that would be known to those skilled in the art.

In the present invention, the medium is supplemented with asparagine and iron. Additional amino acids and nutrients may also be used in accordance with standard cell culture techniques as known to the skilled person, for example to replenish essential amino acids as the cells multiply, replenish an energy source and replenish other essential micronutrients, such as trace elements.

The amount of supplementation required can vary depending on the cellular growth conditions. For example, factors that influence cellular consumption rates, will affect the amount of supplementation that is required to prevent misincorporation. Such factors include, but are not limited to, temperature, osmolality, and pH, as known in the art.

The basal cell culture medium i.e. the medium in which the cell culture is started, prior to any additional supplementation may contain essential amino acids, vitamins (such as folic acid, biotin, thiamine), salts (such as sodium chloride, sodium bicarbonate), metal ions (such as, in the terms of cupric sulphate, Ferric ammonium citrate) all foaming agents (such as Pluronic®) and an energy source (such as glucose or galactose). The particular combination and amounts of each component may vary depending on the cell line, and the recombinant protein to be produced.

Various methods of preparing mammalian cells for production of proteins or polypeptides by fed-batch culture are well known in the art. Generally, the cells are first propagated or expanded in a step-wise procedure until a cell density is reached that is suitable for inoculating the bioreactor in which the method of the invention is to take place.

Such methods of propagation or expansion can be carried out by any of the variety of methods well-known to one of ordinary skill in the art.

In accordance with the present invention, the culture size can be any volume that is appropriate for production of polypeptides. In one embodiment, the volume of the production bioreactor is at least 500 liters. In other embodiments, the volume of the production bioreactor is 1000, 2000, 2500, 5000, 8000, 10,000, 12,000 or 15,000 litres or more, or any volume in between. One of ordinary skill in the art will be aware of and will be able to choose a suitable culture size for use in practicing the present invention.

The cells may be allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more. Embodiments of the present invention may involve maintaining the cell culture over a period of 14 or 17 days.

In accordance with the present invention, the cells may be maintained in the subsequent production phase (after the log phase) until a desired cell density or production titre is reached. In one embodiment, the cells are maintained in the subsequent production phase until the titre to the recombinant polypeptide or protein reaches a maximum. In other embodiments, the culture may be harvested prior to this point. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density.

The cells may be allowed to grow for a defined period of time during the subsequent production phase.

An increased concentration of the amino acids may be added in the basal media prior to the cell culture process (i.e. at day 0) or else supplemented in the feed media in the fed-batch system, on any one or more of day 1, 2, 3, 4, 5, 6, 7, 8, 9, 10, 11, 12, 13 or 14.

In certain cases, it may be necessary to supplement the cell culture during the growth and/or subsequent production phase with nutrients or other medium components that have been depleted or metabolized by the cells. Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components, including the amino acids, may all be added to the cell culture at one time, or they may be provided to the cell culture in a series of additions. In one embodiment of the present invention, the supplementary components are provided to the cell culture at multiple times in proportional amounts. In another embodiment, it may be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture may be 1, 2, 3, 4, 5, 6, 7, 8, 9, 10, 15, 20, 25, 30, 35, 40, 45 or 50% of the volume of the cell culture prior to providing the supplementary components.

In general, it will typically be desirable to isolate and/or purify proteins or polypeptides expressed according to the present invention. In one embodiment, the expressed polypeptide or protein is secreted into the medium and thus cells and other solids may be removed, as by centrifugation or filtering for example, as a first step in the purification process. Further purification may be carried out by any method known to the skilled person.

Once purified, the protein or polypeptide can be formulated as a pharmaceutical composition for administration to a subject, e.g., to treat a disorder, such as an autoimmune disorder or disease.

The foregoing description is to be understood as being representative only and is not intended to be limiting. Alternative methods and materials for implementing the invention and also additional applications will be apparent to one of skill in the art, and are intended to be included within the accompanying claims.

In one aspect of the present invention, the concentration of a metal ion within the cell culture medium may be adjusted in order to control the charge profile of the recombinant protein produced by the culture of cells.

The present invention relates to the field of protein production and in particular to processes for controlling the charge profile (i.e. the level of acidic variants, main peak species and basic variants) of the protein produced by a culture of cells. The charge profile of a recombinant protein produced by a culture of cells may be achieved by certain adjustments that are made to the culture medium or culture conditions. Such adjustments can include concentration of metal ions, concentrations of certain amino acids or adjustments to the pH of the cell culture medium.

In general, fed-batch culture involves a "top-up" of nutrients at certain points during the duration of the cell culture, this may be once a day, once every two days, once every three days or once every four days, or administered after measurement of certain nutrients within the fed-batch culture. The feed medium may be of a different composition for each different feed. The metal ions may be adjusted by way of feed medium (i.e. one or more of the metal ions are incorporated into the feed medium) or may be added independently and separately, e.g. on a different day or on the same day but as a separate supplement.

In embodiments of the present invention, the adjustment of the metal ion may be by way of an increase to one or more metal ions in the cell culture medium, the increase may be of 1%, 5%, 10%, 15%, 20%, 25%, 35%, 50%, 75% or 100% of the amount originally present in the cell culture medium. The metal ion may be included in the cell culture medium from day 0 and then further supplemented into the cell culture medium at any one of day 3, 4, 5, 6, 7, 8, 9, 10, 11, 12, 13 or 14 of the cell culture In some embodiments, the cell culture medium is supplemented with iron to a concentration of from about 0.5 mg/L to about 5.0 mg/L, in addition to any iron already present in the medium. In embodiments of the present invention, the iron may be adjusted by the addition of iron to the cell culture medium in a form of ferric ammonium citrate. In some embodiments, the ferric ammonium citrate or any other suitable iron ion may be added to the cell culture to a concentration of about 0.5 mg/L, about 1.0 mg/L, about 1.5 mg/L, about 2.0 mg/L, about 2.5 mg/L, about 3.0 mg/L, about 3.5 mg/L, about 4.0 mg/L or about 4.5 mg/L, in addition to any iron already present in the medium. In some embodiments, iron may be added to a concentration of about 0.9 mg/L, about 1.7 mg/L, in addition to any iron already present in the medium, or any of the above-mentioned concentrations.

By "to a concentration of" it is meant in additional to any of that metal ion or amino acid already present in the cell culture medium. It is assumed that the cell culture has been depleted of the particular metal ion or amino acid. However, there may be some residual amounts remaining, and the concentration to which the metal ion or amino acid is added does not take into account any residual amount.

In embodiments of the present invention, the cell culture medium may be supplemented with zinc. In some embodiments, the zinc may be in a form of zinc sulphate. In some embodiments, the zinc sulphate or any other suitable form of zinc ion may be added to the medium to a concentration of about 5.0 mM to about 30 mM in addition to any zinc already present in the medium. In other embodiments, the zinc may be added to the cell culture medium to the concentration of about 5.0 mM, about 7.5 mM, about 10.0 mM, about 15.0 mM, about 20.0 mM, or about 25.0 mM, in addition to any zinc already present in the medium. In some embodiments, the zinc may be added to a concentration of about 13.0 mM, about 13.5 mM, about 14 mM, about 14.5 mM or about 15 mM, in addition to any zinc already present in the medium. In other embodiments, the zinc may be added to the culture medium to a concentration of about 14.7 mM, about 5.1 mM or about 10.2 mM, in addition to any zinc already present in the medium, or to any of the above-mentioned concentrations.

In embodiments of the present invention, the metal ion to be adjusted may be selenium. In some embodiments, the selenium may be in the form of sodium selenite. In some embodiments, the selenium may be added to the cell culture medium to an amount of about 5 nM to about 100 nM in addition to any selenium already present in the medium. In other embodiments, selenium may be added to a concentration of about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM or about 100 nM, in addition to any selenium already present in the medium. In some embodiments, the selenium may be added to about 33 nM, about 13 nM, about 25 nM, about 38 nM, or about 76 nM, in addition to any selenium already present in the medium, or to any concentration mentioned above.

In embodiments of the present invention, the metal ion to be adjusted may be copper. In some embodiments, the copper may be in the form of cupric sulphate. In other embodiments, the copper may be added to the culture medium to an amount of about 100 nM to about 1000 nM in addition to any copper already present in the medium In some embodiments, the copper may be added to the culture medium to a concentration of about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, about 1000 nM, in addition to any copper already present in the medium. In embodiments of the present invention, the copper may be added to the culture medium to an amount of about 380 nM, about 159 nM, about 314 nM, about 547 nM, 3 about 53 nM or 706 nM, in addition to any copper already present in the medium.

In embodiments of the present invention, the adjustment of the culture medium is the concentration of an amino acid within the culture medium. The adjustment of the amino acid may be an increase in the amino acid by way of addition to the culture medium of an amino acid at a certain concentration, or on certain days of the culture medium.

In embodiments of the present invention, the amino acid may be asparagine. In some embodiments, the asparagine may be added to the culture medium at a concentration of about 1.5 mM to about 25 mM in addition to any asparagine already present in the medium. In other embodiments, the asparagine may be added at a concentration of about 2 mM, about 3 mM, about 4 mM, about 5 mM, about 7 mM, about 10 mM, about 15 mM, about 20 mM, in addition to any asparagine already present in the medium. In particular, the asparagine may be added at a concentration of about 18.5 mM, about 2.3 mM, about 4.8 mM, about 12.5 mM, about 3.5 mM, about 6.9 mM or about 1.7 mM, in addition to any asparagine already present in the medium.

In embodiments of the present invention, the amino acid to be altered in the culture medium may be tyrosine or cysteine. In some embodiments, the cysteine or tyrosine may be added to the culture medium simultaneously. In other embodiments, the amount of cysteine and tyrosine to be added to the culture medium may be to a concentration of about 1 g/L to about 8 g/L in addition to any cysteine and tyrosine already present in the cell culture medium. In embodiments of the present invention, the amount of cysteine and tyrosine to be added to the cell culture medium may be to about 1 g/l, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, in addition to any cysteine and tyrosine already present in the cell culture medium.

In embodiments of the present invention, another adjustment to the culture medium may be to the pH of the culture medium. In some embodiments, the pH may be increased or decreased. In some embodiments, the pH adjustment may be achieved by the use of carbon dioxide or hydrochloric acid in order to decrease the pH or by sodium bicarbonate or sodium hydroxide in order to increase the pH.

In embodiments of the present invention, the pH is decreased by the use of $CO_2$. In some embodiments, the pH may be decreased to a pH of about 6.5 to about 7.0. In other embodiments, the pH may be decreased to a pH of about 6.8 to about 6.9. In some embodiments, the pH may be decreased to a pH of about 6.88.

EXAMPLES

The following examples were performed in order to increase the biosimilarity of an adalimumab biosimilar to the reference protein, Humira (referred to as RMP, throughout).

Example 1

Previous experiments performed suggested a slight positive impact of zinc and selenium (Zn—Se) on quality data. Indeed, the use of Zn—Se trace elements reduced acidic charge variants while low pH shift increased neutral and decreased basic charge variants. Combining these two conditions was therefore tested as a proof of concept for simultaneously modifying process parameters to obtain a charge profile similar to reference material.

Table 1 shows experimental conditions.

TABLE 1

| Test Conditions | | | |
|---|---|---|---|
| Production medium | Feeds | pH regulation | Legend on graphs |
| standard + ZSCF | Feed containing ZSCF added on day 3, 5, 7 and 10. | free pH between 7.1 and 6.75) | Control |
| standard + Zn-Se | Feed containing Zn-Se added on day 3, 5, 7 and 10. | pH 6.60 ± 0.05 regulated with CO2 | pH 6.7 |

Figure 2:
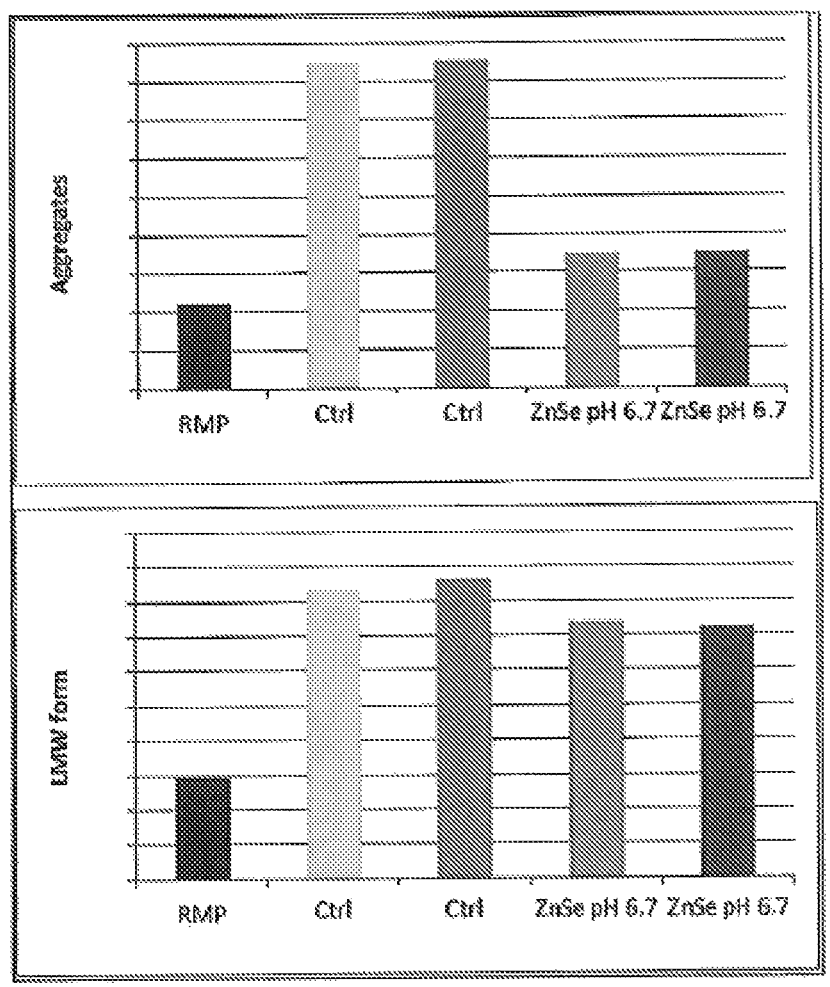
FIG. 2 shows the impact of zinc and selenium of HMW and LMW.

As shown in FIG. 1, Zn—Se and low pH had a positive impact on neutral isoforms (increased), basic isoforms (decreased), mannose-5 (slight increase) and a-fucosylated forms (slight decrease) regarding biosimilarity to RMP. Combining two process parameters, trace element composition and low pH shift, enabled to obtain a charge profile similar to reference material. The level of aggregates and LMW forms were decreased in ZnSe cultures at low pH, getting closer to the reference antibody (FIG. 2).

Example 2

Zinc

To test the impact of Zn, samples were tested with twice the Zn concentration or no Zn in the Feed. Conditions are described in Table 2.

TABLE 2

| Test Conditions | | |
| --- | --- | --- |
| ST | Production medium | Feed |
| Ctrl (1X Zn) | standard + ZSCF | With ZSCF |
| 2X Zn | standard | Without ZSCF |
| 0X Zn | standard | Without ZSCF |

ZSCF = zinc, selenium, copper, iron

Titres tended to be slightly higher in the absence of Zn.

Removing Zn had a slight positive impact on clusters 1 and 2 (decreased) and a negative impact on cluster 4 (increased), on mannose-5 (decreased) and on aggregates (increased) regarding biosimilarity to RMP.

Example 3

Selenium

To test the impact of Se, samples were tested with twice the Se concentration or no Se in the Feed. Conditions are described in Table 3.

TABLE 3

| Test Conditions | | |
| --- | --- | --- |
| ST | Production medium | Feed |
| Ctrl (1X Se) | standard + ZSCF | With ZSCF |
| 2X Se | standard | Without ZSCF |
| 0X Se | standard | Without ZSCF |

Removing Se had a slight positive impact on clusters 4 & 5 (decreased) and on a-fucosylated forms (decreased), and a negative impact on mannose-5 (decreased) regarding biosimilarity to RMP. Removing Se had no impact on the level of aggregates.

Example 4

Copper

To test the impact of Cu, samples were tested with twice the Cu concentration or no Cu in the Feed. Conditions are described in Table 4.

TABLE 4

| Test Conditions | | |
| --- | --- | --- |
| ST | Production medium | Feed |
| Ctrl (1X Cu) | standard + ZSCF | With ZSCF |
| 2X Cu | standard | Without ZSCF |
| 0X Cu | standard | Without ZSCF |

Increasing the Cu concentration had a negative impact on mannose-5 (decrease) and G2 (increase) and a slight positive impact on G0 (decrease) and G1 (increase) regarding biosimilarity to RMP. On the other hand, the level of aggregates was slightly increased in the presence of more Cu.

Example 5

Iron

To test the impact of Fe, ST were tested with twice the Fe concentration or no Fe in the Feed.

Conditions are described in Table 5.

TABLE 5

| Test Conditions | | |
| --- | --- | --- |
| ST | Production medium | Feed |
| Ctrl (1X Fe) | standard + ZSCF | With ZSCF |
| 2X Fe | standard | Without ZSCF |
| 0X Fe | standard | Without ZSCF |

Removing Fe had a positive impact on acidic clusters (decrease of clusters 1 & 2), on neutral cluster 3 (slight increase), on a-fucosylated forms (slight decrease) and G2 (slight decrease) regarding biosimilarity to RMP. Aggregate levels, on the other hand, were increased.

Example 6

No Trace Elements

To globally test the impact of trace elements (TE), controls containing all 4 TE (namely, zinc, selenium, copper and iron) ZSCF were compared to samples containing no TE. Conditions are described in Table 6.

TABLE 6

| Test Conditions | | | |
| --- | --- | --- | --- |
| ST | Production medium | Feed | Cys Tyr |
| Ctrl | standard + ZSCF | With ZSCF | yes |
| No TE | standard | Without ZSCF | yes |

Unpredictably from the above examples, removing TE had a negative impact on basic clusters (clusters 4 & 5 increased), on mannose-5 (decreased), and on G2 forms (decreased) regarding biosimilarity to RMP. Therefore, TE were selected to be included into the cell culture process.

Figure 3:
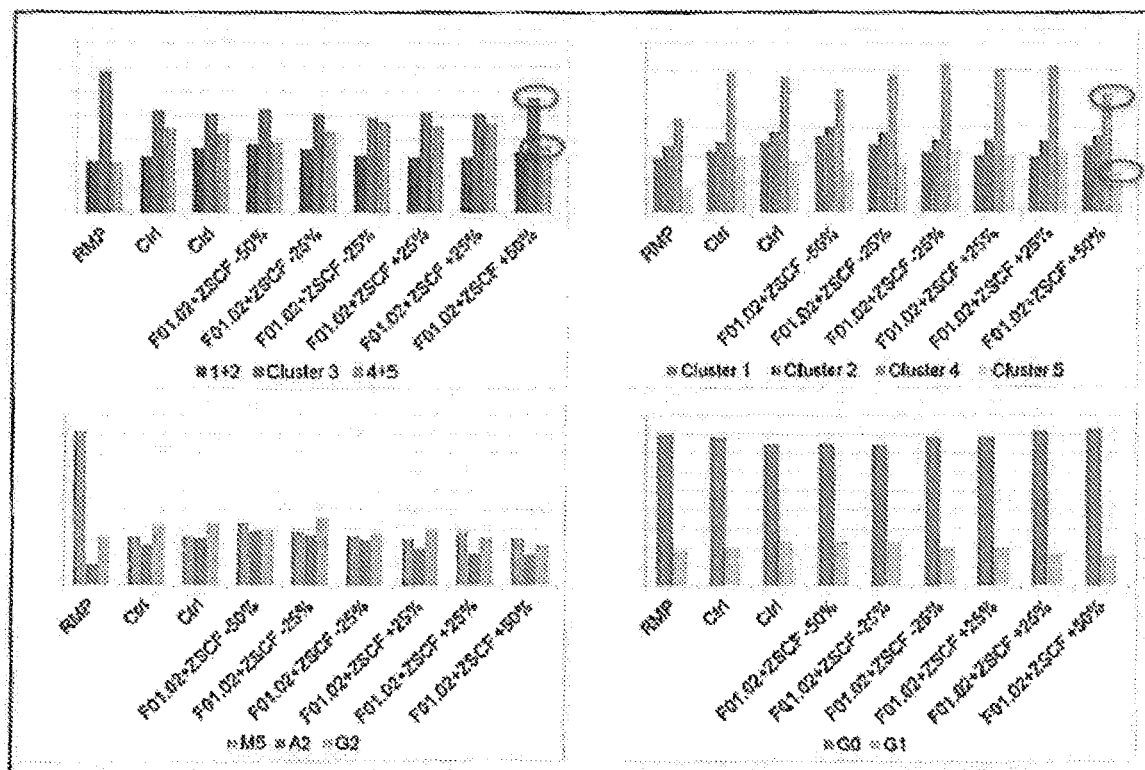
FIG. 3 shows the impact on charge profile of the presence and absence of trace elements.

Results are shown in FIG. 3.

Two cell culture processes were selected, process 1 and 2. The concentrations of ZSCF at days 0, 3, 5, 7 and 10 of each process are shown below. These concentrations levels were found to result in the adalimumab biosimilar falling within the "biosimilar corridor" of levels of characteristics of the reference protein.

| Cell culture processes 1: | | | |
|---|---|---|---|
| | day 0 | day 3 | day 5, 7 and 10 |
| Iron (Ferric Ammonium Citrate): | 3 mg/L | 0.9 mG/L | 1.7 mg/L |
| Zinc (Zinc Sulfate): | 14.7 uM | 5.1 uM | 10.2 uM |
| Selenium (Sodium selenite): | 33 nM | 13 nM | 25 nM |
| Copper (Cupric Sultate): | 380 nM | 159 nM | 314 nM |

| Cell culture process 2: | | | |
|---|---|---|---|
| | day 0 | day 3 | day 5, 7 and 10 |
| Iron (Ferric Ammonium Citrate): | 3 mg/L | 0.9 mG/L | 1.7 mg/L |
| Zinc (Zinc Sulfate): | 14.7 uM | 5.1 uM | 10.2 uM |
| Selemium (Sodium selenite): | 33 nM | 13 nM | 25 nM |
| Copper (Cupric Sulfate): | 380 nM | 159 nM | 314 nM |

The invention claimed is:

1. A cell culture method of modifying the charge profile of a Tumor Necrosis Factor-alpha (TNF α) binding protein produced by cell culture in a cell culture medium, wherein the method comprises (a) culturing cells that express a TNFα binding protein that is an antibody comprising a light chain sequence having at least 90% identity with SEQ ID NO: 1 and a heavy chain sequence having at least 90% identity with SEQ ID NO: 2 in a cell culture medium for one or more days and (b) making adjustments to at least two cell culture condition conditions, wherein an adjustment comprises addition of Cu, Fe, Se, and Zn ions to the cell culture medium, wherein Fe is added to a concentration of about 0.5 mg/L to about 5.0 mg/L, in addition to any Fe already present in the cell culture medium, Cu is added to a concentration of about 100 nM to about 1000 nM, in addition to any Cu already present in the cell culture medium, Zn is added to a concentration of about 1 μM to about 30 μM, in addition to any Zn already present in the cell culture medium, and Se is added to a concentration of about 5 nM to about 100 nM, in addition to any Se already present in the cell culture medium, and a further adjustment comprises adding $CO_2$ to decrease the pH of the cell culture medium, and wherein the adjustments occur on one or more days of culturing the cells, whereby the adjustments to the cell culture conditions result in the modification of the charge profile of the binding protein.

2. The method according to claim 1, wherein the cells are CHO-S cells.

3. The method according to claim 1, wherein the Cu, Fe, Se and Zn ions are added by way of adding a feed medium comprising the ions to the culture medium on one or more of day 3, 4, 5, 6, 7, 8, 9, 10, 11, 12, 13 or 14 of culturing the cells.

4. The method according to claim 1, wherein the cell culture medium is serum-free.

5. A cell culture method of producing a protein comprising: (a) growing a host cell that expresses the protein in a cell culture medium for one or more days, (b) expressing the protein in the host cell, wherein the protein is an antibody comprising a light chain sequence having at least 90% identity with SEQ ID NO: 1 and a heavy chain sequence having at least 90% identity with SEQ ID NO: 2, (c) making adjustments to at least two cell culture conditions, wherein an adjustment is adding Cu, Fe, Se, and Zn ions to the cell culture medium, wherein Fe is added to a concentration of about 0.5 mg/L to about 5.0 mg/L, in addition to any Fe already present in the cell culture medium, Cu is added to a concentration of about 100 nM to about 1000 nM, in addition to any Cu already present in the cell culture medium, Zn is added to a concentration of about 1 µM to about 30 µM, in addition to any Zn already present in the cell culture medium, and Se is added to a concentration of about 5 nM to about 100 nM, in addition to any Se already present in the cell culture medium, and a further adjustment comprises adding $CO_2$ to decrease the pH of the cell culture medium, wherein adjustments occur on one or more days of the growing of the host cell, whereby the adjustments to the cell culture conditions result in the modification of the charge profile of the protein, and (d) purifying the protein from the cell culture; wherein the duration of the cell culture method is longer than 24 hours.

6. The method according to claim 5, wherein the host cell is a CHO-S cell.

7. The method according to claim 5, wherein the addition of the Cu, Fe, Se and Zn ions is by way of adding a feed medium comprising the ions to the culture medium on one or more of day 3, 4, 5, 6, 7, 8, 9, 10, 11, 12, 13 or 14 of the growing of the host cell.

* * * * *

SEQUENCE LISTING

```
<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variabe region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

```
<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
```

```
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                               321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tgagggccg attcaccatc tccagagaca cgccaagaa ctccctgtat     240 ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                   363
```